US006258955B1

(12) United States Patent
Meagher

(10) Patent No.: US 6,258,955 B1
(45) Date of Patent: Jul. 10, 2001

(54) PROCESS FOR PREPARING 2-PIPERIDINEETHANOL COMPOUNDS

(75) Inventor: Timothy P. Meagher, Indianapolis, IN (US)

(73) Assignee: Reilly Industries, Inc., Indianapolis, IN (US)

( * ) Notice: Subject to any disclaimer, the term of this patent is extended or adjusted under 35 U.S.C. 154(b) by 0 days.

(21) Appl. No.: 09/385,670

(22) Filed: Aug. 27, 1999

Related U.S. Application Data

(60) Provisional application No. 60/098,316, filed on Aug. 28, 1998.

(51) Int. Cl.$^7$ .................................................. C07D 211/02
(52) U.S. Cl. ............................................................ 546/185
(58) Field of Search ............................................. 546/185

(56) References Cited

U.S. PATENT DOCUMENTS

| | | | |
|---|---|---|---|
| 3,717,593 | * 2/1973 | Zondler et al. ...................... | 528/118 |
| 4,581,456 | 4/1986 | Barnett ................................ | 546/185 |
| 4,587,369 | * 5/1986 | Cosyns et al. ....................... | 585/259 |
| 5,478,535 | 12/1995 | Fierz et al. .......................... | 422/205 |
| 6,080,863 | 6/2000 | Matson et al. ....................... | 546/185 |

FOREIGN PATENT DOCUMENTS 1315260  12/1961 (FR).

OTHER PUBLICATIONS

Broser et al. "2–(2–piperidinyl)ethanol" CA 89:146768, 1976.*
Lavagnino et al. "Conidine—synthesis . . . " J. Am. Chem. Soc. v.82, p.2609–2613, 1960.*
V. Bockelheide et al., *J. Am. Chem. Soc.,* Amine Oxides. Cyclic Quaternary Salts and their Decomposition, vol. 80, pp. 2217–2220 (1958).
Robert R. Burtner et al., *J. Am. Chem. Soc.,* Antispasmodics. III. Diarylacetic Acid Esters of Some Pyridyl and Piperidyl Alkanols. vol. 69, pp. 630–633 (1947).
P.H.M.R. Cramers et al., *Chemical Engineering Science,* Hydrodynamics And Mass Transfer Characteristics Of A Loop–Venturi Reactor With A Downflow Liquid Jet Ejector, vol. 47, No. 13/14, pp. 3557–3564 (1992), Printed in Great Britain.
P.H.M.R. Cramers et al., *Chemical Engineering Science,* Influence of the Gas Density on the Gas Entrainment Rate and Gas Hold–Up In Loop–Venturi Reactors, vol. 47, No. 9–11, pp. 2251–2256, (1992), Printed in Great Britain.
P.H.M.R. Cramers et al., *The Chemical Engineering Jornal,* Hydrodynamics and local mass transfer characteristics of gas–liquid ejectors, 53 pp. 67–73 (1993).
Morris–Freifelder et al., *J. Org. Chem.,* Hydrogenation in the Pyridine Series. III. Formation of a By–Product in the Nickel–Catalyzed Reduction of 2–(2–Hydroxyethyl) pyridine, vol. 30, pp. (1965).

Morris Freifelder et al., *J. Org. Chem.,* Hydrogenation of Substituted Pyridines with Rhodium on Carbon Catalyst, vol. 27, pp. 284 (1962).
Morris Freifelder et al., *J. Org. Chem.,* Reductions with Ruthenium. II. Its Use in the Hydrogenation of Pyridines, vol. 26, pp. 3805–3808, (1961).
T.S. Hamilton et al., *J. Am. Chem. Soc.,* Reduction of Pyridine Hydrochloride and Pyridonium Salts By Means of Hydrogen and Platinum–Oxide Platinum Black. XVIII, vol. 50, pp. 2260–2263 (1928).
Edward R. Lavagnino et al., *J. Am. Chem. Soc.,* Conidine–Synthesis, Polymerization and Derivatives, vol. 82, pp. 2609–2613 (1960). See especially page 2610 flow chart.
Gunter M. Leuteritz et al., Reprinted from *Hydrocarbon Processing,* Loop reactors: Better gas/liquid contact, (1976).
C.S. Marvel et al., *J. Am. Chem. Soc.,* Local Anesthetics Derived From 2–(Beta–Hydroxyethyl)–Piperidine, vol. 51, pp. 915–917 (1929).
T. R. Norton et al., *J. Am. Chem. Soc.,* The Synthesis of Some Substituted 8–Aminoquinolines, vol. 68, pp. 1572–1576 (1946).
Edgar A. Steck et al., *J. Am. Chem. Soc.,* Pyridazine Derivatives. V. Some Ethers and Thioethers Derived from 3,6–Dichloropyridazine, vol. 81, pp. 6511–6514 (1959).
C. W. Tullock et al., *J. Am. Chem. Soc.* Piperidine Derivatives. XIV. Local Anesthetics Derived from α–Picoline, vol. 61, pp. 961–964 (1939).
Prof. dr. ir. L.L. van Dierendonck et al., $6^{th}$ *European Conference on MIXING,* Scale–Up of G–L Reactions Made Simple With Loop Reactors, pp. 287–295 (May 24–26, 1988), Held in Pavia, Italy.
Roger Adams et al., *J. Amn. Chem. Soc.,* The Use of Platinum–Oxide Platinum Black in the Catalytic Reduction of Aromatic Hydrocarbons, vol. 50, pp. 1970–1973 (Jul. 1928).
Cramers et al., Unpublished, Prediction of the mass transfer characteristics of gas/liquid ejectors, 6 pages total, (Approximately 1997).
Cramers et al., Unpublished, Process Intensification With Buss Loop Reactors, 8 pages total, (Approximately 1997).

(List continued on next page.)

*Primary Examiner*—Ceila Chang
(74) *Attorney, Agent, or Firm*—Woodard, Emhardt, Naughton, Moriarty & McNett

(57) ABSTRACT

Described are preferred processes for producing 2-piperidineethanol compounds by hydrogenation of corresponding 2-pyridineethanol compounds. The preferred processes are conducted in the presence of an amine other than said reactant or product, and a hydrogenation catalyst preferably comprising a noble metal catalyst such as ruthenium or palladium or oxides thereof loaded to a high level in the system. The catalyst is preferably provided on a heterogeneous support, and most preferred processes are conducted using both controlled temperature conditions and high levels of catalyst to minimize the formation of deleterious byproducts.

35 Claims, No Drawings

OTHER PUBLICATIONS

R.J. Malone et al., *Chemical Engineering Progress,* Loop Reactor Technology Improves Catalytic Hydrogenations, pp. 53–59 (Jun. 1980).

Dr. G. Leuteritz, *Process Engineering,* CA 80:097, 764q, pp. 62–63 (Dec. 1973).

W. Koenigs, Ber., 35, 1355 (1902).

Landenburg, Ber., 22, 2583 (1889).

M. Rink et al., *Arch. Pharm.,* CA 60: 15873 (e), pp. 74–82 (1960).

William Carruthers, et al., *J. Chem. Soc.,* Penkin Trans. 1, (8), pp. 2251–2253 (1988).

Broser et al., Database CAS on STN, *Chemical Abstracts* (Columbus, OH, USA) AN 89:146788, '2–(2–piperidinyl)ethanol' RO 61609, see whole article. Abstract Only (1976).

Nishimura et al., Database CAPLUS on STN, *Bull Chem. Soc.,* Selective homogeneous hydrogenation of 3–oxo–1, 4–diene steroids, vol. 46, No. 1, pp. 279–282, (1973). Abstract Only.

Ponomarev V.D. et al., *Chem. Abst.,* Hydrogenation of nitrogen heterocyles on ruthenium catalysts, vol. 78, No. 1, (Jan. 8, 1973) (Columbus, OH, USA) the abstract No. 4101s, geterogen. Katal. Reakts. Poluch. Prevrashch. Geterotsikl. Soedin. 1971, 155–9 (Russ). Abstract Only.

* cited by examiner

2-PIPERIDINEETHANOL COMPOUNDS

REFERENCE TO RELATED APPLICATION

This application claims priority upon U.S. patent application Ser. No. 60/098,316 filed Aug. 28, 1998, which is hereby incorporated by reference in its entirety.

BACKGROUND

The present invention relates generally to the preparation of 2-piperidineethanol compounds, and more specifically to improved processes for preparing 2-piperidineethanol compounds involving the hydrogenation of corresponding 2-pyridineethanol compounds in the presence of hydrogenation catalysts.

As further background, 2-(2-Hydroxyethyl)piperidine (also known as 2-piperidineethanol or 2-ethanolpiperidine) and related piperidine compounds are useful inter alia as intermediates to pharmacological agents and insect repellents. Various processes for preparing 2-piperidineethanol and related compounds have been described. For example, several references in the literature describe the preparation of 2-piperidineethanol via the catalytic hydrogenation of 2-pyridineethanol. Illustratively, T. S. Hamilton et al., *J. Am. Chem. Soc.*, Vol. 50, pp. 2260–2263 (1928), describes the preparation of 2-piperidineethanol hydrochloride by the catalytic reduction of 2-pyridineethanol hydrochloride in ethanol at room temperature in the presence of a platinum-oxide platinum black catalyst. A number of other references describe similar or related reductions in the presence of platinum oxide catalysts in mixed solvents containing acetic acid and either water or ethanol. See, R. R. Burtner et al., *J. Am. Chem. Soc.*, Vol. 69, pp. 630–633 (1947); E. A. Steck et al., *J. Am. Chem. Soc.*, Vol. 81, pp. 6511–6514 (1959); and M. Rink et al., 60 *Arch. Pharm.*, pp. 74–82 (1960).

Other catalyst and solvent combinations have also been tried. As examples, M. Freifelder et al., *J. Org. Chem.*, Vol. 26, pp. 3805–3808 (1961), describes a hydrogenation of 2-pyridineethanol in methanol in the presence of a ruthenium dioxide catalyst to produce 2-piperidineethanol. In later-reported work, M. Freifelder et al., *J. Org. Chem.*, Vol. 62, pp. 284–286 (1962) describe the preparation of 2-piperidineethanol by hydrogenating the corresponding pyridine in an ethanol solvent in the presence of a rhodium on carbon catalyst. E. R. Lavagnino et al., *J. Am. Chem. Soc.*, Vol. 82, pp. 2609–2613 (1960), describes a hydrogenation of 2-pyridineethanol with a palladium on carbon catalyst in water to form the corresponding piperidine.

2-piperidineethanol has also been formed by the reductive cleavage of appropriate cyclic salts of pyridine-N-oxide, as disclosed by V. Boekelheide et al, *J. Am. Chem. Soc.*, Vol. 80, pp. 2217–2220 (1958).

In light of the background in this area, there has remained a need and demand for effective commercial routes to 2-piperidineethanol compounds. Such routes will desirably provide high yields and selectivities, while employing readily available starting materials and minimizing the formation of undesired byproducts that may interfere with subsequent purification or use of the 2-piperidineethanol products. The embodiments of the present invention address these needs.

SUMMARY OF THE INVENTION

It has been discovered that 2-piperidineethanol compounds can be prepared in good yields and selectivities while minimizing problematic formation of corresponding N-methylated 2-piperidineethanol byproducts, by hydrogenating corresponding 2-pyridineethanol compounds in a reaction medium including an effective amount of another amine, a high catalyst loading, and temperatures controlled to minimize byproduct formation. Accordingly, one preferred embodiment of the invention provides processes for producing 2-piperidineethanol compounds via the hydrogenation of a corresponding 2-pyridineethanol in the presence of at least about 10 mole % of another amine relative to the 2-pyridineethanol and a metal or metal oxide hydrogenation catalyst provided at a high level in the system, typically at least about 0.15 grams of catalyst (considered as the metal alone) per mole of 2-pyridineethanol compound, and desirably utilizing hydrogen pressures of at least about 500 psig and/or moderate temperatures which minimize byproduct formation, for example about 90° C. to about 120° C. Noble metal or noble metal oxide catalysts, especially ruthenium and oxides thereof (e.g. ruthenium dioxide), provide highly preferred catalysts for such processes, and the other amine is advantageously piperidine or a substituted piperidine employed as a sole or co-solvent. It has been found that the presence of the other amine in this system, combined with the use of high catalyst loadings, provides for advantageous processes with dramatically reduced formation of problematic byproducts in the reaction, particularly corresponding N-methyl-2-(2-hydroxyethyl)piperidine compounds. In more preferred processes, the other amine also serves as a solvent in the system, either alone or in combination with another solvent such as an organic solvent or water. Preferred other amines include substituted or unsubstituted piperidine, especially piperidine itself.

As to other preferences in the above-described processes, ruthenium on carbon provides a catalyst of particular advantage, and the processes are desirably conducted in the presence of hydrogen at a pressure of at least 1500 psig, typically in the range of 1500 to 5000 psig. The temperature during the hydrogenations more preferably falls within the range of about 100° C. to about 120° C., and when heterogeneous supports are used in the catalyst they are typically loaded with the metal or metal oxide to a level of about 3% to about 10% by weight. When used as the other amine, substituted piperidines can generally include any substituent that does not interfere with the hydrogenation reaction and consequent formation of the 2-piperidineethanol product. Lower alkyl-substituted piperidines are suitable for these purposes. In addition, it will be typical to include the other amine in an amount of about 10 mole % to 1000 mole % relative to the 2-pyridineethanol starting material. Any two or more of these preferences can also be combined to provide advantageous processes, and all such combinations are contemplated as being a part of the present invention.

Another preferred embodiment of the present invention provides a method for the manufacture of a 2-piperidineethanol compound, which includes conducting a series of reactions using a hydrogenation catalyst, each reaction comprising hydrogenating a corresponding 2-pyridineethanol compound in the presence of the hydrogenation catalyst and hydrogen at a pressure of at least about 500 psi. In between reactions in the series, the catalyst is contacted with an amine containing solvent for a period of time effective to condition the catalyst to improve its performance in a subsequent reaction. Such catalyst "pickling" processes have shown to unexpectedly maintain a high catalyst activity over a series of reactions.

The present invention provides processes for preparing 2-piperidineethanol compounds by the catalytic hydrogenation of corresponding 2-pyridineethanol compounds, with high yield and selectivity, and minimal formation of problematic N-methyl-2-(2-hydroxyethyl)piperidine byproducts. The preferred processes can be conducted using readily available equipment and starting materials, and under conditions attractive for commercial implementation. These and other features and advantages of the present invention will be apparent from the descriptions herein.

DESCRIPTION OF THE PREFERRED EMBODIMENTS

For the purpose of promoting an understanding of the principles of the invention, reference will now be made to certain preferred embodiments thereof and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, the present invention provides improved processes for preparing 2-piperidineethanol compounds. Preferred processes of the invention involve the hydrogenation of a corresponding 2-pyridineethanol compound in the presence of another amine and a hydrogenation catalyst. The other amine differs in chemical structure from both the 2-pyridineethanol and 2-piperidineethanol starting and product compounds, and is present in an amount effective to significantly suppress the formation of N-methyl derivatives of the 2-piperidineethanol compound, which for most purposes will be an amount of at least about 10 mole % relative to the 2-pyridineethanol starting compound. Most preferred processes are conducted under relatively mild temperature conditions with high levels of catalyst, so as to further minimize the formation of deleterious by-products.

As to the reactants themselves, the starting materials will include a substituted or unsubstituted 2-pyridineethanol compound. In this regard, the substituents present on the compound can be those typical in the art which survive the conditions of hydrogenation or otherwise do not interfere with the hydrogenation. Preferred starting materials in accordance with the invention include those of the formula (I):

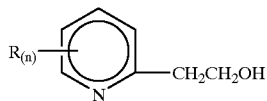

wherein n can be 0, 1, 2, 3 or 4, and R is an organic group having 1 to about 20 carbon atoms. When present, the group or groups R are preferably alkyl, more preferably lower alkyl (i.e. having from 1 to about 5 carbon atoms).

The amine used in the present processes will be one other than the pyridineethanol compound, or its corresponding piperidineethanol product. For example, the amine can be a primary, secondary or tertiary amine. Further, it can be cyclic or non-cyclic. Illustrative amines thus include mono-, di- or trialkyl amines, wherein the alkyl groups are preferably lower alkyl; substituted and unsubstituted piperidine compounds, wherein any substitution is preferably lower alkyl. Suitable amines also include aromatic amines, for example including aniline, aromatic heterocycles such as pyridine or lower-alkyl-substituted pyridines, and the like. In accordance with the present invention, substituted and unsubstituted piperidine compounds are highly preferred, particularly piperidine itself.

As to the amount of the other amine, it will preferably be used in an amount of at least 10 mole % relative to the ethanol-pyridine starting compound. Typically, the amine will be used in a molar ratio of between 10% and 1000 mole % relative to the pyridineethanol starting material. The amine can serve as the solvent or as a co-solvent in the system if desired, and when used as co-solvent it will be combined with another solvent in which it is miscible, for example an organic solvent such as an alcohol (e.g. methanol or ethanol) or water.

As indicated above, processes of the present invention employ a hydrogenation catalyst which is effective to hydrogenate the pyridine ring to form a corresponding piperidine ring. For these purposes, noble metal or noble metal oxide catalysts are preferred, particularly palladium and ruthenium or oxides thereof. Ruthenium and ruthenium dioxide are especially preferred catalysts for use in the invention.

Catalysts used in the inventive processes are preferably but not necessarily provided on a heterogeneous support, and in this case they will desirably be loaded on the support to at least 3% by weight, typically in the range of 3% to 10% by weight. More preferably, supported catalyst loadings will be at least 5% by weight. As indicated, forms other than supported forms can be used, for example ruthenium oxide or similar unsupported catalyst forms may be used. Given the teachings herein, one skilled in the art will be readily able to select and utilize a suitable catalyst.

In more preferred reactions, the catalyst will be incorporated in the reaction mixture at a high level, for example in an amount of at least 0.15 grams/mole (considered as the metal alone) of 2-pyridineethanol starting compound, more preferably at least about 0.2 grams/mole of 2-pyridineethanol starting compound, typically falling in the range of about 0.2 grams/mole to about 1 gram/mole.

As to the conditions of reacting, processes of the invention will in general be conducted at a temperature of about 90° C. to about 200° C. It is especially preferred that the processes be conducted at temperatures no greater than about 120° C. for example about 90° C. to about 120° C. As demonstrated in the examples below, at these temperatures, the formation of deleterious by-products is minimized or substantially eliminated.

As to the reaction pressure, hydrogen pressures of at least about 500 psig are preferably utilized, more preferably at least about 1000 psig. In the most preferred reactions, the hydrogen pressure will be at least 1500 psig, typically in the range of 1500 psig to 10000 psig, and more typically in the range of 1500 psig to 5000 psig.

Reactions in accordance with the invention will preferably be well mixed by agitation or other means. In addition, heat exchange means can be incorporated in the reactor for removing heat generated by the reaction. These means may be provided within and/or external of the reaction zone. For example, suitable loop reactors incorporating heat exchange means for heat removal are commercially available from Buss AG, Pratteln, Switzerland. Suitable reactors incorporating internal heat exchange elements within the reaction zone are provided by Biazzi hydrogenating systems available from Biazzi SA, Montreux, Switzerland, and described in its product literature entitled "Biazzi Hydrogenation Technology" and/or in U.S. Pat. No. 5,478,535.

As to matters of sequence, in one preferred mode of carrying out the processes, all materials except for the 2-pyridineethanol compound are charged to the reactor, and the 2-pyridineethanol compound is then dosed to the reactor over time. In this fashion, additional control of heat generation is possible, which is particularly important when the equipment utilized lacks adequate means for dissipating heat such as those described above. The reactants can, however, be charged in any suitable order or fashion, including all together, the latter being preferably conducted where the reactor utilized has heat exchange elements for heat removal as discussed above.

Products of preferred processes of the invention conducted using pyridineethanols of formula (I) above will have a corresponding piperidine structure (II):

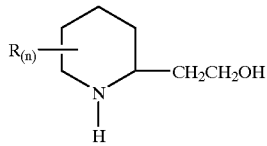

wherein n and R are defined as above in conjunction with formula (I). The reaction will preferably be conducted under conditions effective to provide reaction products constituted less than 1% by weight of the corresponding N-methylated 2-piperidineethanol byproduct (N-methyl-2-(2-hydroxyethyl)piperidine), more preferably less than about 0.5% by weight.

Product recovery steps can be conventional. For example, the catalyst can be filtered from the reacted mixture, which can then be distilled to recover the 2-piperidineethanol product. The 2-piperidineethanol product can be conventionally used, for example in the preparation of pharmacologically active compounds, insect repellents, or the like.

In addition, the catalyst can be regenerated and reused in a subsequent reaction. Preferred regeneration cycles include heating in an amine-containing solvent system as described above in the presence of hydrogen, preferably at a pressure of at least 500 psig, and at a temperature of at least about 90° C., typically in the range of 90° C. to 200° C. The catalyst will be heated under these conditions for a sufficient period of time to regenerate the catalyst activity. Typical regeneration times will be at least one-half hour, more typically one to twenty-four hours, most typically about one to twelve hours.

Still further, it has been discovered that high catalyst activity can be maintained by a process in which in between reactions, the catalyst is contacted with an amine containing solvent system for an extended duration. This process is referred to herein as "pickling", and is preferably conducted in addition to any regeneration cycle as described immediately above. The pickling process need not be conducted under heated conditions or in the presence of hydrogen, although both of these are also possible. Illustrative pickling processes can be conducted from ambient temperature to less than about 90° C., preferably from ambient temperature to less than about 50° C. The amine solvent can be any of those identified above, and is preferably piperidine or pyridine. The pickling is desirably conducted in the presence of hydrogen or another inert gas such as nitrogen, which can be used at pressures near atmospheric or at superatmospheric pressures. Generally, the duration of the pickling process will be sufficient to maintain a consistent, high activity for the catalyst throughout the series of reactions underway. Usually, the duration will be at least about two hours, with the maximum duration dictated by economic factors relating to the effective utilization of the catalyst. Durations of two to five-hundred hours will be typical. In carrying out the manufacture of 2-piperidineethanol compounds using processes incorporating pickling, it may be advantageous to maintain two or more catalyst charges which are alternately used in a reactor and/or to maintain two or more reactors, each with its own catalyst charge, which are alternately used to manufacture the desired compound. In this manner, one reaction can be underway while the alternate catalyst charge (s) is undergoing a pickling process. These and other variations in the manufacturing process will be apparent to one of ordinary skill in the art.

For the purposes of providing additional illustrations of the present invention and its advantages, the following specific examples are provided. These examples are illustrative and not limiting of the invention. In these examples, the following abbreviations are used: EP=2-pyridineethanol; PE=2-piperidineethanol; PEP=1-[2-(2-piperidinyl)ethyl]-piperidine; and MPA=N-methyl-2-(2-hydroxyethyl) piperidine; $C_5H_{10}N$=piperidine.

EXAMPLE 1

Low Pressure Hydrogenations with Various Catalysts

Low pressure hydrogenations were carried out by charging 250 mL of solvent, 246 g of 2-pyridineethanol, and catalyst into a pressure vessel capable of agitation, agitating the resulting mixture and pressurizing the vessel and its contents to 500 psi with hydrogen. Under constant hydrogen pressure and continued agitation, the reaction mixture was heated to 150° C. until hydrogen uptake ceased. The pressure vessel and its contents were cooled, vented and the catalyst removed with vacuum filtration. Upon distillation of the filtrate, 2-piperidineethanol was obtained and analyzed on two separate gc columns (6' CW 20M 160° C. and 15M DB-1 80° C.→220° C.@ 16° C./m capillary column) to provide product yield and composition of the distillate. The results are provided in Table I.

TABLE I

| Catalyst, g | Solvent, mL | Time, hrs | % Yield | % 2-EP | % 2-PE | % MPA | % PEP |
|---|---|---|---|---|---|---|---|
| 5% Ru/C, 10 | $H_2O$ | 7.9 | 42.3 | 44.28 | 44.87 | 4.35 | 0.10 |
| 5% Ru/C, 30 | $C_5H_{10}N$ | 7.7 | 53.0 | 21.14 | 67.25 | 0.23 | 5.93 |
| 5% Ru/Al$_2$O$_3$, 30 | $H_2O$ | 2.5 | 56.1 | 0 | 82.55 | 16.04 | 0.19 |
| 5% Ru/Al$_2$O$_3$, 30 | $C_5H_{10}N$ | 5.3 | 64.6 | 0.03 | 88.31 | 0.35 | 8.54 |
| 5% Ru/C, 15 | $H_2O$ | 5.8 | 53.0 | 0.06 | 88.82 | 4.89 | 1.06 |
| 5% Pd/C, 30 | $H_2O$ | 6.0 | 53.0 | 0 | 81.96 | 16.59 | 0.03 |
| 5% Pd/C, 30 | $C_5H_{10}N$ | 4.0 | 73.8 | 3.76 | 88.99 | 0.41 | 1.82 |
| Sponge Ni, 30 | $H_2O$ | 9.3 | 31.6 | 19.18 | 54.64 | 23.02 | 0.27 |
| 5% Pd/Al$_2$O$_3$, 30 | $C_5H_{10}N$ | 8.9 | 48.6 | 36.21 | 60.24 | 0.59 | 0.60 |
| RuO$_2$, 2.5 | $H_2O$ | 3.5 | 59.1 | 0 | 82.80 | 14.67 | 0.32 |
| RuO$_2$, 2.5 | $C_5H_{10}N$ | 3.8 | 71.5 | 0 | 91.01 | 0 | 5.30 |
| 5% Ru/C, 30 | $H_2O$ | 3.1 | 68.3 | 0.04 | 90.40 | 8.59 | 0.09 |
| 5% Ru/C, 30 | $C_5H_{10}N$ | 5.0 | 69.3 | 21.33 | 74.73 | 0 | 1.01 |

TABLE I-continued

| Catalyst, g | Solvent, mL | Time, hrs | % Yield | % 2-EP | % 2-PE | % MPA | % PEP |
|---|---|---|---|---|---|---|---|
| 5% Pt/Al$_2$O$_3$, 30 | H$_2$O | 9.4 | 61.6 | 17.31 | 74.70 | 5.80 | 0.27 |
| 5% Pt/C, 30 | H$_2$O | 7.8 | 41.9 | 36.06 | 55.57 | 4.39 | 0.29 |
| 5% Ru/C, 10 | C$_5$H$_{10}$N | 7.5 | 50.9 | 39.20 | 54.60 | 0.38 | 4.01 |
| Raney Ni, 30 | H$_2$O | 4.9 | 46.3 | 2.25 | 74.41 | 19.03 | 0.36 |
| RuO$_2$, 0.8 | H$_2$O | 8.2 | 42.5 | 0.23 | 73.52 | 20.84 | 0.47 |
| RuO$_2$, 0.8 | C$_5$H$_{10}$N | 8.2 | 73.0 | 1.74 | 89.13 | 0.48 | 4.72 |
| 5% Pd/C, 10 | C$_5$H$_{10}$N | 9.2 | 64.1 | 16.15 | 77.40 | 0.15 | 1.36 |
| 5% Ru/Al$_2$O$_3$, 10 | H$_2$O | 5.2 | 44.7 | 0 | 77.88 | 20.77 | 0.13 |
| 5% Ru/Al$_2$O$_3$, 10 | C$_5$H$_{10}$N | 7.1 | 67.3 | 0 | 93.46 | 0.46 | 4.46 |
| 5% Ru/C, 30 | C$_5$H$_{10}$N, 200 H$_2$O, 50 | 7.7 | 67.1 | 5.37 | 81.60 | 0.27 | 9.94 |
| 5% Pd/Al$_2$O$_3$, 30 | H$_2$O | 8.7 | — | 41.70 | 41.69 | 22.87 | 0.03 |
| 5% Ru/C, 10 | H$_2$O | 8.3 | 62.8 | 2.76 | 83.14 | 13.70 | 0 |
| 10% Ru/C, 15 | C$_5$H$_{10}$N | 7.8 | 65.9 | 11.55 | 81.34 | 0.08 | 3.94 |
| 5% Ru/C, 30 | C$_5$H$_{10}$N, 125 H$_2$O, 125 | 7.6 | 74.7 | 0.93 | 86.60 | 0.46 | 10.30 |
| 5% Ru/C, 30 | C$_5$H$_{10}$N, 50 H$_2$O, 200 | 7.9 | 66.7 | 0.22 | 88.51 | 1.05 | 8.56 |

EXAMPLE 2

Low Pressure Hydrogenations with Ruthenium Catalysts

Low pressure hydrogenations were carried out by charging solvent, 2-pyridineethanol, and different quantities of various ruthenium supported catalysts into a pressure vessel capable of agitation, agitating the resulting mixture and pressurizing the vessel and its contents to 500 psi with hydrogen. Under constant hydrogen pressure and continued agitation, the reaction mixture was either heated to a constant reaction temperature or heated to an initial reaction temperature with incremental increases of 10° C. to a final reaction temperature. Reactions were allowed to continue until hydrogen uptake ceased. The pressure vessel and its contents were cooled, vented and the catalyst removed with vacuum filtration. Upon distillation of the filtrate, 2-piperidineethanol was obtained and analyzed on a gc column (6' CW 20M 160° C.) to provide product yield and composition of the distillate. The results are provided in Table II.

EXAMPLE 3

Low Pressure Hydrogenations with Ruthenium on Carbon

Hydrogenations were carried out by charging solvent, 246 g of 2-pyridineethanol, and varying amounts of 5% ruthenium on carbon (5% Ru/C) into a pressure vessel capable of agitation, agitating the resulting mixture and pressurizing the vessel and its contents to 500 psi with hydrogen. Under constant hydrogen pressure and continued agitation, the reaction mixture was heated to 150° C. until hydrogen uptake ceased. The pressure vessel and its contents were cooled, vented and the catalyst removed with vacuum filtration. Upon distillation of the filtrate, 2-piperidineethanol was obtained and analyzed on two separate gc columns (6' CW 20M 160° C. and 15M DB-1 80° C.→220° C.@ 16° C./m capillary column) to provide product yield and composition of the distillate. The results are provided in Table III.

TABLE II

| Catalyst, g | EP(g) | Temp. (° C.) | Solvent, mL | Time (hrs) | % Yield | % EP | % PE | % MPA | % PEP |
|---|---|---|---|---|---|---|---|---|---|
| 5% Ru/C, 2.5 | 61.5 | 150 | H$_2$O, 60 | 7.8 | 61.3 | 0.7 | 88.9 | 10.4 | 0 |
| 5% Ru/C, 2.5 | 61.5 | 150 | H$_2$O, 30 C$_5$H$_{10}$N, 30 | 4.9 | 56.6 | 24.5 | 75.4 | 0 | 0 |
| 5% Ru/C, 2.5 | 61.5 | 150 | H$_2$O, 50 C$_5$H$_{10}$N, 100 | 7.0 | 67.7 | 1.2 | 97.3 | 1.5 | 0 |
| 5% Ru/C, 2.5 | 61.5 | 110 | H$_2$O, 60 | 4.5 | 82.3 | 0.3 | 98.4 | 1.2 | 0 |
| 5% Ru/C, 2.5 | 61.5 | 150 | H$_2$O, 60 | 4.8 | 71.2 | 0.6 | 92.1 | 6.9 | 0 |
| 5% Ru/C, 2.5 | 61.5 | 60–90 | C$_6$H$_{12}$, 10 | 8.0 | 84.1 | 4.7 | 95.0 | 0.1 | 0 |
| 5% Ru/C, 2.5 | 61.5 | 45–65 | H$_2$O, 60 | 6.4 | 82.2 | 1.1 | 98.5 | 0 | 0 |
| 5% Ru/C, 2.5 | 61.5 | 60–95 | EtOH, 60 | 6.5 | 75.7 | 13.3 | 86.0 | 0 | 0 |
| 5% Ru/C, 4.9 | 12.3 | 60 | EtOH, 50 | 1.2 | 76.5 | 4.3 | 95.6 | 0 | 0 |
| 5% Ru/C, 10 | 246 | 150 | H$_2$O, 250 | 8.3 | 62.8 | 2.3 | 88.6 | 8.9 | 0 |
| 5% Ru/C, 10 | 246 | 150 | C$_5$H$_{10}$N, 250 | 9.8 | 38.8 | 47.1 | 46.8 | 3.2 | 0 |
| 5% Ru/C, 30 | 246 | 150 | C$_5$H$_{10}$N, 250 | 5.0 | 69.3 | 0 | 93.2 | 6.5 | 0 |
| 5% Rh/Al$_2$O$_3$, 2.5 | 61.5 | 50–100 | H$_2$O, 60 | 6.8 | 89.3 | 1.9 | 98.0 | 0 | 0 |
| 5% Rh/Al$_2$O$_3$, 2.5 | 61.5 | 50–100 | C$_6$H$_{12}$, 60 | 9.0 | 72.5 | 17.1 | 82.8 | 0 | 0 |
| 5% Rh/Al$_2$O$_3$, 2.5 | 61.5 | 30–55 | EtOH, 60 | 7.3 | 71.0 | 18.0 | 82.0 | 0 | 0 |

TABLE III

| 5% Ru/C, g | Solvent, mL | Time (hrs) | % Yield | % 2-EP | % 2-PE | % MPA | % PEP |
|---|---|---|---|---|---|---|---|
| 10 | $H_2O$, 250 | 7.9 | 42.3 | 44.28 | 48.87 | 4.35 | 0.10 |
| 10 | $C_5H_{10}N$, 250 | 7.5 | 50.9 | 39.20 | 54.60 | 0.38 | 4.01 |
| 10 | $H_2O$, 125 $C_5H_{10}N$, 125 | 8.4 | 62.0 | 19.77 | 78.64 | 0.32 | 0 |
| 30 | $H_2O$, 250 | 5.8 | 68.4 | 0.06 | 88.82 | 4.89 | 1.06 |
| 30 | $C_5H_{10}N$, 250 | 7.7 | 53.1 | 21.14 | 67.25 | 0.23 | 5.93 |
| 30 | $C_5H_{10}N$, 200 $H_2O$, 50 | 7.7 | 62.1 | 5.37 | 81.6 | 0.27 | 9.94 |
| 30 | $C_5H_{10}N$, 50 $H_2O$, 200 | 8.3 | 69.6 | 0.11 | 91.72 | 1.07 | 6.35 |
| 30 | $C_5H_{10}N$, 125 $H_2O$, 125 | 7.6 | 74.7 | 0.93 | 86.6 | 0.46 | 10.27 |

EXAMPLE 4

Low and High Pressure Hydrogenations with Ruthenium Oxide

Hydrogenations were carried out by charging solvent, when utilized, 246 g of 2-pyridineethanol, and 2.5 g of ruthenium oxide ($RuO_2$) into a pressure vessel capable of agitation, agitating the resulting mixture and pressurizing the vessel and its contents to 500 psig or 1000 psig with hydrogen. Under constant hydrogen pressure and continued agitation, the reaction mixture was heated to the reaction temperature until hydrogen uptake ceased. The pressure vessel and its contents were cooled, vented and the catalyst removed with vacuum filtration. Upon distillation of the filtrate, 2-piperidineethanol was obtained and analyzed on two separate gc columns (6' CW 20M 160° C. and 15M DB-1 80° C.→220° C.@ 16° C./m capillary column) to provide product yield and composition of the distillate. The results are provided in Table IV. Hydrogenations were also carried out with recycled $RuO_2$ catalyst under the conditions described above. The results of these reactions utilizing recycled catalyst are provided in Table V.

TABLE IV

| Solvent, mL | Time (hrs) | Temp. (° C.) | Press. (psig) | % Yield | % 2-EP | % 2-PE | % MPA | % PEP |
|---|---|---|---|---|---|---|---|---|
| $C_5H_{10}N$, 250 | 8.4 | 115 | 500 | 82.8 | 9.34 | 88.60 | 0.19 | 0.58 |
| $C_5H_{10}N$, 250 | 3.8 | 150 | 500 | 71.5 | 0 | 91.01 | 0 | 5.30 |
| $C_5H_{10}N$, 250 | 6.6 | 105 | 1000 | 91.9 | 0.06 | 98.17 | 0.17 | 0.41 |
| $C_5H_{10}N$, 250 | 5.0 | 125 | 1000 | 90.6 | 0.03 | 98.03 | 0.05 | 0.76 |
| $C_5H_{10}N$, 250 | 3.0 | 150 | 1000 | 81.4 | 0.09 | 95.70 | 0.09 | 3.16 |
| $C_5H_{10}N$, 200 $H_2O$, 50 | 5.8 | 125 | 500 | 84.6 | 1.35 | 94.77 | 0.10 | 2.43 |
| $C_5H_{10}N$, 200 $H_2O$, 50 | 6.0 | 115 | 500 | 86.5 | 4.40 | 92.68 | 0.42 | 1.50 |
| None | 6.8 | 125 | 500 | 88.5 | 0.08 | 97.02 | 2.39 | 0 |
| None | 8.2 | 120 | 500 | 89.3 | 0.08 | 97.62 | 1.68 | 0 |
| None | 7.5 | 115 | 500 | 85.3 | 4.35 | 93.55 | 1.23 | 0 |
| None | 2.7 | 125 | 1000 | 92.8 | 0.03 | 98.90 | 0.66 | 0.05 |

TABLE V

| Solvent, mL | Time (hrs) | Temp. (° C.) | Press. (psig) | % Yield | % 2-EP | % 2-PE | % MPA | % PEP |
|---|---|---|---|---|---|---|---|---|
| $C_5H_{10}N$, 250 | 6.8 | 125 | 500 | 86.9 | 0.28 | 95.67 | 0.17 | 1.60 |
| $C_5H_{10}N$, 250 | 8.0 | 125 | 500 | 86.7 | 1.36 | 93.18 | 0.09 | 2.65 |
| $C_5H_{10}N$, 250 | 8.1 | 125 | 500 | 87.2 | 0.89 | 92.99 | 0.52 | 2.86 |
| $C_5H_{10}N$, 250 | 8.4 | 125 | 500 | 85.3 | 1.62 | 92.51 | 0.68 | 3.32 |
| $C_5H_{10}N$, 250 | 9.0 | 215 | 500 | 78.I | 9.73 | 84.77 | 0.65 | 3.02 |

EXAMPLE 5

High Pressure Hydrogenations with 5% Ruthenium on Carbon in Various Solvents Utilizing Catalyst Recycle A pressure vessel capable of agitation was charged with catalyst and solvent, purged three times with hydrogen, pressurized to 1500 psi with hydrogen, and heated with agitation to 120° C. for two (2) hours. The resulting slurry was cooled to 50° C. and vented. 2-pyridineethanol was charged to the reactor, and the reactor and its contents were pressurized to 1500 psi with hydrogen and heated with agitation to 110° C. for seventeen (17) hours. The reaction mixture was cooled to 100° C., the reactor vented, and the reaction mixture filtered. The filtrate was analyzed by gc to determine reaction products and unreacted starting material.

Subsequent reactions (Runs 2–15) were carried out with recovered catalyst by charging solvent to the catalyst and the heel of the previous run, pressurizing the reactor to 1500 psi with hydrogen and heating the slurry with agitation to 120° C. for two (2) hours. The reactor and its contents were cooled to 50° C., vented, and the reactor charged with the pyridineethanol. The reactor was pressurized to 1500 psi with hydrogen and its contents heated with agitation to 110° C. for three (3) to twenty-four (24) hours. The reaction mixture was cooled to 100° C., the reactor vented, and the reaction mixture filtered. The filtrate was analyzed by gc to determine reaction products and unreacted starting material. The results of Runs 1–16 are provided in Table VI.

TABLE VI

| Run | Solvent, g | Time (hrs) | Temp (° C.) | Sel. | % Yield | % 2-EP | % 2-PE | % MPA | % PEP |
|---|---|---|---|---|---|---|---|---|---|
| 1 | $C_5H_{10}N$, 100 | 17 | 110 | 96.2 | 95.9 | 0.3 | 95.9 | 0.0 | 1.4 |
| 2 | $C_5H_5N$, 100 | 17 | 110 | 95.8 | 88.9 | 7.2 | 88.9 | 0.1 | 1.1 |
| 3 | n-butylamine, 100 | 17 | 110 | 89.6 | 89.3 | 0.4 | 89.3 | 0.4 | 1.5 |
| 4 | triethylamine, 100 | 3 | 180 | 72.0 | 68.0 | 5.5 | 68.0 | 5.2 | 0.2 |
| 5 | $C_5H_{10}N$, 100 | 17 | 110 | 94.5 | 94.4 | 0.2 | 94.4 | 0.2 | 1.5 |
| 6 | triethylamine, 100 | 17 | 110 | 96.3 | 96.0 | 0.3 | 96.0 | 0.5 | 0.6 |
| 7 | aniline, 100 | 17 | 110 | 87.8 | 87.5 | 0.3 | 87.5 | 0.8 | 5.8 |
| 8 | $H_2O$, 100 | 17 | 110 | 89.9 | 89.9 | 0.1 | 89.9 | 2.5 | 0.0 |
| 9 | MeOH, 100 | 17 | 110 | 93.6 | 93.4 | 0.3 | 93.4 | 2.2 | 0.1 |
| 10 | $H_2O$, 100 | 17 | 110 | 91.3 | 91.0 | 0.3 | 91.0 | 3.0 | 0.0 |
| 11 | MeOH, 100 | 17 | 110 | 91.5 | 91.3 | 0.2 | 91.3 | 2.3 | 0.1 |
| 12 | $C_5H_5N$, 100 | 17 | 110 | 92.4 | 92.2 | 0.1 | 92.2 | 0.1 | 1.6 |
| 13 | $C_5H_5N$, 100 | 24 | 110 | 93.8 | 93.6 | 0.2 | 93.6 | 0.1 | 1.8 |
| 14 | $NH_4OH/H_2O$, 100 | 17 | 110 | 85.7 | 83.0 | 3.1 | 83.0 | 2.1 | 0.5 |
| 15 | 42% $NaOH/H_2O$, 100 | 17 | 110 | 29.4 | 23.9 | 18.7 | 23.9 | 0.2 | 0.0 |

EXAMPLE 6

Hydrogenations with Intervening Pickling of Catalyst

Two additional sets of runs with catalyst recycle were performed using generally the reaction procedures described in Example 5. In the first set of runs, tabulated in Table VII, subsequent runs were carried out with recovered catalyst by charging solvent to the catalyst and the heel of the previous run, pressurizing the reactor to 1500 psi with hydrogen and heating the slurry with agitation to 120° C. for two (2) hours, and then proceeding with the next run, as in Example 5. In the second set of runs, set forth in Table VIII, a similar two-hour regeneration was performed after each run, followed by pickling the catalyst/solvent/heel mixture at ambient temperature for the period of time indicated.

TABLE VII

Catalyst Recycle Without Pickling

| Run | Solvent | Pickle (hrs) | Reaction Temp (° C.) | Reaction Time (hrs) | % Yield | % 2-EP | % 2-PE | % MPA | % PEP |
|---|---|---|---|---|---|---|---|---|---|
| 1 | piperidine | 0 | 120 | 17 | 93 | 0.09 | 93.3 | 0.08 | 2.91 |
| 2 | piperidine | 0 | 120 | 24 | 91 | 0.02 | 90.5 | 0.21 | 3.93 |
| 3 | piperidine | 0 | 120 | 10 | 87 | 5.7 | 86.9 | 0.35 | 2.22 |

TABLE VIII

Catalyst Recycle With Pickling

| Run | Solvent | Pickle Time (hrs) | Reaction Temp (° C.) | Reaction Time (hrs) | % Yield | % 2-EP | % 2-PE | % MPA | % PEP |
|---|---|---|---|---|---|---|---|---|---|
| 1 | piperidine | 15 | 120 | 10 | 93 | 0.01 | 93.4 | 0.11 | 2.26 |
| 2 | piperidine | 14.5 | 120 | 9 | 94 | 0.07 | 93.6 | 0.12 | 2.06 |
| 3 | piperidine | 14.5 | 120 | 7 | 95 | 0.16 | 94.6 | 0.13 | 1.46 |
| 4 | piperidine | 14 | 120 | 7 | 93 | 0.07 | 93.2 | 0.15 | 1.72 |
| 5 | piperidine | 63 | 120 | 7 | 94 | 0.08 | 94.2 | 0.11 | 1.50 |

As the results in Tables VII and VIII show, the reactions are benefited dramatically by pickling the catalyst in between runs. Illustratively, run 3 in Table VII (no pickling) was terminated at 10 hours, and the yield (86.9%) indicates that the reaction was not complete. In contrast, runs 3–5 in Table VIII (pickling) were essentially complete after only seven hours of reacting.

In addition, still further runs were carried out in the set of Table VIII, wherein pyridine was substituted for piperidine. Pickling and subsequent reaction (in which the pyridine solvent is also hydrogenated, to piperidine), yielded similarly good results. Further, in these subsequent runs it was demonstrated that the initial two-hour catalyst regeneration could be conducted at ambient temperature and/or with hydrogen at low pressure (20 psi) or with nitrogen (200 or 20 psi), all while achieving similarly good reactions. Also, from the subsequent runs it was concluded that after a prior series of runs with pickling, the pickling procedure could be reduced in frequency (e.g. every few runs) or eliminated, while still achieving good results.

While various preferred embodiments of the invention have been described in detail above, the same is to be considered illustrative in nature. All modifications and additions as would occur to one of ordinary skill in the field to which this invention pertains are contemplated as being a part of this invention and are desired to be protected. In addition, all publications cited herein are indicative of the level of ordinary skill in the art, and are hereby incorporated by reference in their entirety as if each had been individually incorporated by reference where cited and fully set forth.

What is claimed is:

1. A process for preparing a 2-piperidineethanol compound, comprising:

hydrogenating a corresponding 2-pyridineethanol compound in a reaction medium in the presence of a hydrogenation catalyst, at least about 10 mole % of another amine relative to the 2-pyridineethanol compound, and hydrogen at a pressure of at least about 500 psig, and wherein said hydrogenation catalyst contains a noble metal or noble metal oxide, said noble metal or noble metal oxide being present in said reaction medium in an amount of at least 0.15 grams per mole of 2-pyridineethanol compound.

2. The process of claim 1, wherein said hydrogenating is conducted at a temperature of about 90° C. to no greater than about 120°.

3. The process of claim 2, wherein the catalyst is ruthenium on carbon.

4. The process of claim 2, conducted in the presence of hydrogen at a pressure of 1500 to 10000 psi.

5. The process of claim 2, wherein said hydrogenating is conducted at a temperature of about 100° C. to about 120° C.

6. The process of claim 1, wherein the catalyst is ruthenium loaded to a level of about 3% to about 10% on a heterogeneous support.

7. The process of claim 6, wherein the catalyst is ruthenium loaded to a level of at least about 5% on a heterogeneous support.

8. The process of claim 7, wherein the catalyst is ruthenium on carbon.

9. The process of claim 1, wherein the catalyst is a ruthenium or palladium catalyst.

10. The process of claim 1, wherein the catalyst is a ruthenium catalyst.

11. The process of claim 1, wherein the other amine is a heterocycle containing at least one nitrogen atom in its heterocyclic ring.

12. The process of claim 11, wherein the other amine is a substituted or unsubstituted piperidine compound.

13. The process of claim 12, wherein the other amine is piperidine or a lower-alkyl-substituted piperidine.

14. The process of claim 13, wherein the other amine is piperidine.

15. The process of claim 1, wherein the other amine is included in an amount of about 10 mole % to about 1000 mole % relative to the 2-pyridineethanol compound.

16. The process of claim 1, wherein the reaction medium also includes water.

17. The process of claim 16, wherein the reaction medium includes a substituted or unsubstituted piperidine compound and water.

18. The process of claim 17, wherein the reaction medium includes piperidine and water.

19. The process of claim 1, wherein prior to said hydrogenating, said hydrogenation catalyst has been pickled in an amine containing solvent.

20. A process for preparing 2-piperidineethanol, comprising:

hydrogenating 2-pyridineethanol in the presence of a catalyst comprising a noble metal or noble metal oxide, said hydrogenating being conducted at a temperature of about 90° C. to no greater than 120° C. and in the presence of another amine and hydrogen at a pressure of at least 1000 psi.

21. The process of claim 20, wherein the catalyst is ruthenium loaded to a level of about 3% to about 10% on a heterogeneous support.

22. The process of claim 20, wherein the other amine is a heterocycle containing at least one nitrogen atom in its heterocyclic ring.

23. The process of claim 22, wherein the other amine is a substituted or unsubstituted piperidine compound.

24. The process of claim 23, wherein the other amine is piperidine or a lower-alkyl-substituted piperidine.

25. The process of claim 24, wherein the other amine is piperidine.

26. A method for the manufacture of a 2-piperidineethanol compound, which comprises:

conducting a series of reactions using a hydrogenation catalyst, each reaction comprising hydrogenating a corresponding 2-pyridineethanol compound in the presence of the hydrogenation catalyst and hydrogen at a pressure of at least about 500 psi; and pickling the hydrogenation catalyst in an amine containing solvent in between reactions in said series.

27. The method of claim 26, wherein the hydrogenation catalyst comprises ruthenium.

28. The method of claim 27, wherein the hydrogenation catalyst comprises ruthenium loaded on a heterogeneous support to at least 3% by weight.

29. The method of claim 26, wherein the 2-piperidineethanol compound is 2-piperidineethanol, and the corresponding 2-pyridineethanol compound is 2-pyridineethanol.

30. The method of claims 26, wherein said hydrogenating is conducted in a solvent containing an amine in an amount of at least about 10 mole % relative to the 2-pyridineethanol compound.

31. The method of claim 26, wherein said hydrogenating is conducted at a temperature of about 90° C. to no greater than about 120° C., in the presence of hydrogen at a pressure of at least 1000 psig, and wherein said catalyst is present in said reaction medium in an amount of at least 0.15 grams per mole of 2-pyridineethanol compound.

32. The method of claim 26, wherein two or more charges of catalyst are alternately used in said series of reactions.

33. The process of claim 1, wherein said other amine is a primary, secondary, or tertiary amine.

34. A process for treating a hydrogenation catalyst utilized in a process for preparing a 2-piperidineethanol compound by hydrogenating a corresponding 2-pyridineethanol compound in a reaction medium in the presence of a hydrogenation catalyst, said process comprising the step of contacting the hydrogenation catalyst with an amine-containing solvent in the presence of hydrogen.

35. The process of claim 34, wherein said contacting is under heated conditions in the presence of hydrogen at a pressure of at least 500 psig.

* * * * *